United States Patent [19]
Pins et al.

[11] Patent Number: 5,229,164
[45] Date of Patent: Jul. 20, 1993

[54] PROCESS FOR PRODUCING INDIVIDUALLY DOSED ADMINISTRATION FORMS

[75] Inventors: Heinrich Pins, Eberbach/Baden; Christiane Schmitz, Lauffen a. N., both of Fed. Rep. of Germany

[73] Assignee: Capsoid Pharma GmbH, Lauffen a. N., Fed. Rep. of Germany

[21] Appl. No.: 474,206

[22] PCT Filed: Dec. 12, 1986

[86] PCT No.: PCT/EP86/00740
§ 371 Date: Sep. 9, 1987
§ 102(e) Date: Sep. 9, 1987

[87] PCT Pub. No.: WO87/03805
PCT Pub. Date: Jul. 2, 1987

Related U.S. Application Data

[63] Continuation of Ser. No. 111,790, Sep. 9, 1987, abandoned.

[30] Foreign Application Priority Data

Dec. 19, 1985 [DE] Fed. Rep. of Germany ....... 3545090

[51] Int. Cl.⁵ .............................................. A61K 9/00
[52] U.S. Cl. ............................................ 427/3; 264/5; 264/264
[58] Field of Search .............. 264/328.11, 264, 5; 425/6, 377, 563.6; 222/432, 1, 146.2, 146.5, 55.1; 427/3

[56] References Cited

U.S. PATENT DOCUMENTS

| | | | |
|---|---|---|---|
| 2,345,917 | 4/1944 | Coffman | 425/563 |
| 2,790,201 | 4/1957 | Eilbracht et al. | 425/6 |
| 2,796,033 | 6/1957 | Feinstein | 107/54 |
| 3,341,087 | 9/1967 | Rosin et al. | 222/422 |
| 3,608,150 | 9/1971 | Laufer et al. | 425/563 |
| 3,832,252 | 8/1974 | Higuchi | 156/86 |

FOREIGN PATENT DOCUMENTS

| | | |
|---|---|---|
| 360655 | 1/1981 | Austria . |
| 1017322 | 10/1957 | Fed. Rep. of Germany . |
| 1904070 | 8/1970 | Fed. Rep. of Germany . |
| 1947684 | 4/1971 | Fed. Rep. of Germany . |
| 7411652 | 7/1974 | Fed. Rep. of Germany . |
| 2710307 | 9/1977 | Fed. Rep. of Germany . |
| 2726427 | 1/1979 | Fed. Rep. of Germany ...... 425/563 |
| 3224619 | 5/1983 | Fed. Rep. of Germany . |
| 3230602 | 2/1984 | Fed. Rep. of Germany . |
| 7311945 | 11/1973 | France . |
| 2530421 | 1/1984 | France . |
| 8219233 | 1/1984 | France . |
| 284791 | 12/1952 | Switzerland . |
| 1042944 | 9/1965 | United Kingdom . |
| 1510772 | 5/1978 | United Kingdom . |

Primary Examiner—Bernard Nozick
Attorney, Agent, or Firm—Helfgott & Karas

[57] ABSTRACT

Process for producing individually dosed administration forms, in which a carrier material containing active substances plastic at elevated temperature, together with conventional additives is applied to a stationary or moving substrate or introduced into blisters or cavities produced from films and as a result the formulation material is brought into an administration form and a formulation material with a softening point range above the body temperature is heated to above the latter and is dosed under pressure with a viscosity of more than 3,000 mPa.s, together with administration forms obtainable by said process. They can be obtained simply, economically and with good quality.

25 Claims, 4 Drawing Sheets

PROCESS FOR PRODUCING INDIVIDUALLY DOSED ADMINISTRATION FORMS

This is a continuation of application Ser. No. 111,790, filed Sep. 9, 1987, now abandoned.

TECHNICAL FIELD

The invention relates to a process for producing individually dosed administration forms, in which a formulation material containing active agents which are plastic at elevated temperature and conventional additives is placed on a stationary or moving substrate or in blisters or cavities produced from films and as a result the formulation material is transferred, accompanied by cooling, into an administration form, as well as to the administration forms obtainable by this process.

PRIOR ART

The conventional, widely used, solid administration forms for the administration of medicaments, dietetics and the like are essentially tablets, dragees, soft and hard gelatin capsules. These administration forms all require in a first stage shaping and in a second stage product packaging, which must meet the requirements of the product (e.g. stability) and the wishes of the consumer (e.g. attractiveness).

This stepwise production of a product up to the final packaging is disadvantageous from the cost standpoint when it is possible to obtain usable products no longer requiring separate shaping and instead are given their particular shape by the packaging or as a result of the consistency thereof through simple, dosing application to a substrate "run" to the desired shape and are then solidified. If simpler ways are possible, two-stage procedures must be looked upon as disadvantageous.

It could be assumed that processes for filling forms are known and widely used and no longer have any novelty value. As will be shown hereinafter, the patent literature contains information on this subject, which also applies to the pharmaceutical field.

DE-AS 1 017 322 describes a process in which use is made of a combined mould and pack for moulding and despatching ready for sale and use blanks of medicaments and similar materials, such as suppositories, pastilles and the like. However, two or more hinged-interconnected mould parts are required, each of which must have more than half the thickness of the subsequent moulded part to be effective in the sense of the known proposal. It is not possible to separate a packed individual dose.

The entire length of the sliding cover must be removed from the pack to permit the requisite folding apart of the mould parts for removing the shaped blanks. This necessarily leads to a contamination of the fragments which have remained in the pack due to dirt and microorganisms. DE-AS 1 017 322 also mentions the filling of the mould parts with the aid of a moulding frame, which is intended to permit a filling of the mould up to the edge. Material which projects and then solidifies after moulding can be scraped off and reused. This filling process cannot be pharmaceutically relevant as a result of its dosing inaccuracy, because the medicaments resulting therefrom would not meet present day demands.

The same applies with regards to the proposal for producing packaged administration forms according to German patent 1 947 684. This proposal constitutes a further development of the prior art of DE-AS 1 017 322, in that the aforementioned moulding frame is replaced by a perforated film, which is intended to ensure cleaner filling of the individual moulds. Here again it is a complex, discontinuous and hygienically dubious procedure, which cannot therefore be satisfactory.

The procedure of moulding fat-containing materials has been further developed in the meantime. Thus, for some time, separatable hollow forms or cavities preshaped from films have been filled with melted suppository material. After passing through a cooling tunnel, the previously open form is sealed. Approximately 25,000 suppositories per hour can be produced by using costly, automated machines. It is a disadvantageous of this process, which is limited to fats with melting points below 40° C., that solid substances may sediment during the moulding and cooling process due to the low viscosity of the melted fat. Another danger is constituted by the change to the physical parameters of the fats used due to melting and recooling. There can be melting point changes and the moulded articles may be brittle.

Attempts have been made to transfer the knowledge acquired in connection with the moulding of suppositories to orally administrable dosage forms. Thus, DE-OS 27 10 307 describes a process for producing and packaging solid pharmaceutical dosage units, which are produced in tablet form in that the mixture is applied to a continuously moving belt made from a different material and which has tablet-like depressions. The carrier substance can be constituted by fats, fatty mixtures, as well as other lipoid substances and components, whose melting point is above 37° C. and preferably above 43° C. The important statement of DE-OS 27 10 307 for the purposes of the present invention is in the sentence that the melted mixture of carrier substance and active component is "poured" into the depressions with or without a measuring device. This can only mean that it is a low-viscosity, liquified substance mixture which can still be poured, whilst the risk of sedimentation of solids is inherent therein and leads to limitations with respect to the carrier substances used.

The description of the process of DE-OS 27 10 307 does not extend beyond the use of relatively low-melting fats and waxes, which can serve as a matrix for the active substance or substances. It is left open as to how these products can be removed without breaking from the depressions of the foils, how they taste as fats and what release rates are to be expected. At least no product is as yet known which has achieved market success.

The knowledge of the aforementioned patent literature and related publications reveals that the results have not been satisfactory. Firstly the use of carrier substances is limited to those materials which, as fats or waxes, have a relatively low melting point and secondly the introduction of the material into the moulds is limited to pouring processes.

SUMMARY OF THE INVENTION

On the basis of this prior art, the problem of the present invention is to so further develop the same that it is possible to process other, more advantageous matrix materials than those described in DE-OS 27 10 307 and which are highly viscous at temperatures above body temperature and supply viscosity values of more than 3000 mPa.s, in a simple and economic manner to high-quality, individually dosed administration forms, without the aforementioned, disadvantageous sedimentation tendency of suspended components.

According to the invention this problem is solved in that the formulation material is based on a sol:gel ratio with a softening range above body temperature and is heated to above body temperature and is dosed with a viscosity of more than 3000 mPa.s under pressure action.

BRIEF DESCRIPTION OF THE DRAWINGS

FIG. 1b is a side view of the product of FIG. 1a;

FIG. 2d shows a sectional view and FIGS. 2b to 2g show perspective views of the administration forms of FIG. 2a;

FIG. 3b is a perspective view of the administration form produced from the respective cavity of FIG. 3a;

FIG. 3c is a sectional view of the administration form produced from another cavity of FIG. 3a;

FIGS. 3d to 3h are perspective views of administration forms extracted from the respective cavities of FIG. 3a.

DETAILED DESCRIPTION OF THE PREFERRED EMBODIMENTS

Thus, the essence of the invention is that the formulation material to be dosed has a softening point range above body temperature. Thus, the inventively dosed formulation material has the nature of a thermoplastic or plastomer. Thus, these are materials which are essentially not permanently shapeable at normal temperature. Thus, these can be materials which are hard or even brittle at normal temperature, which reversibly soften when heat is supplied and can be mechanically relatively easily shaped, in order to ultimately pass into the state of a viscous material at higher temperatures. It is always necessary to fulfil the requirement of the invention that the formulation material has a softening range above body temperature. It is obvious that this requirement or characteristic of the thermoplastic material is essentially determined by the carrier material to be described in greater detail hereinafter. However, additives, such as plasticizing additives and the like also have an influence thereon. It is a further requirement of the invention that the minimum viscosity of the carrier material is 3000 mPa.s.

However, this viscosity value can be greatly exceeded, e.g. up to more than 50,000 mPa.s or even more than 100,000 mPa.s and can extend up to 500,000 mPa.s.

The process according to the invention can be particularly successfully performed with dosing equipment able to manage viscosities of 500,000 mPa.s, because it is not possible to use simple pumping and pouring processes.

The dosing equipment can in particular be constituted by heatable units operating at high pressure, which have controllable valves, against which the piston or geared pumps build up a uniform high pressure. Through time-precisely limited opening of the valve an always constant quantity of the formulation material to be filled is discharged. Incorporated nozzles or filling needles ensure a clean filling of the hollow forms/cavities and blisters or an exact application to substrates. The pressure under which dosing takes place is generally above 2 bar and is dependent on the viscosity of the heated formulation material to be dosed. It is advantageously between 10 and 70 bar, particularly between 35 and 55 bar.

Figure 4:
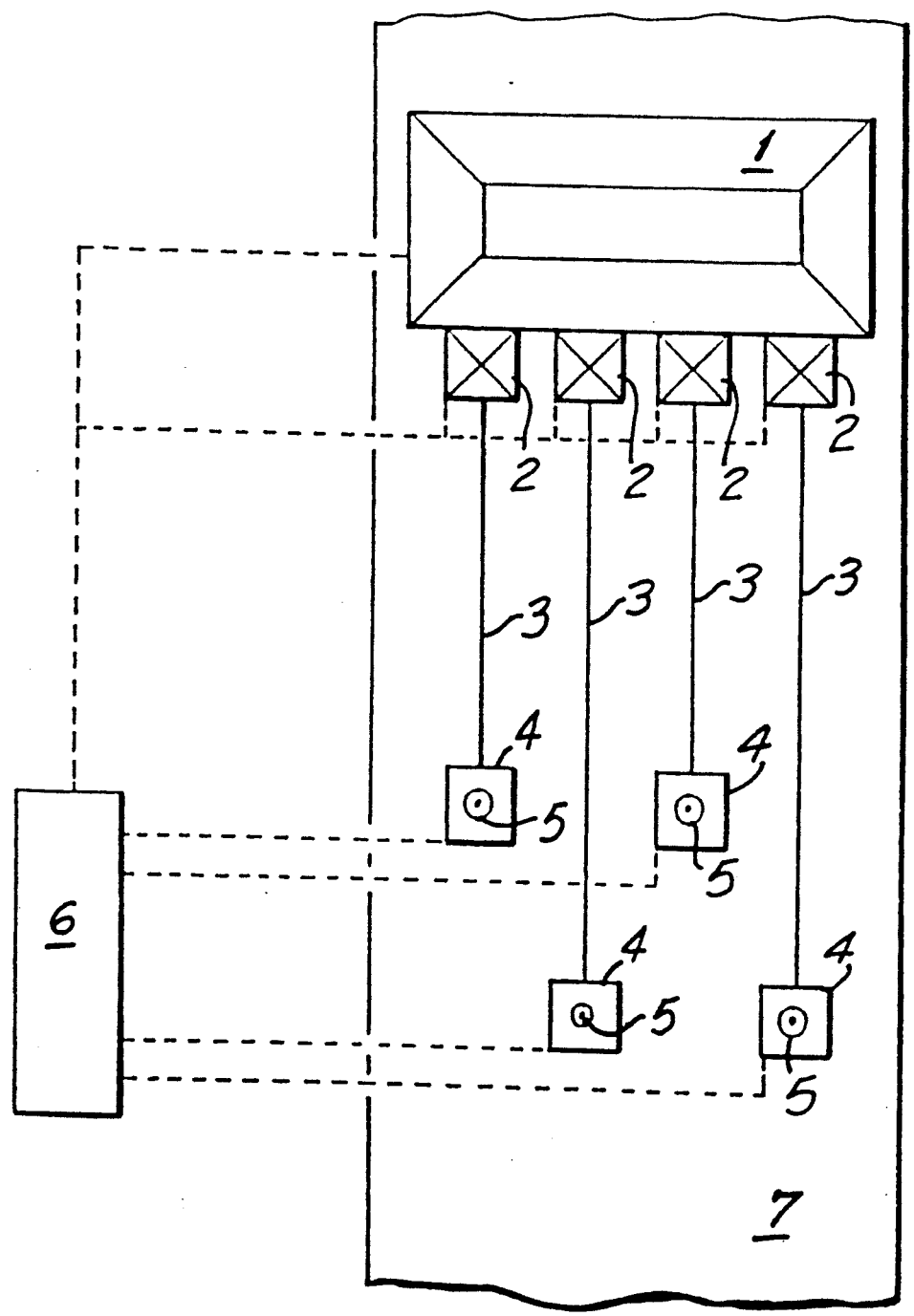
FIG. 4 is a schematic view of a filling equipment for making administration forms according to the invention.

Basic equipment of the presently described type of filling plants is e.g. supplied in the firms Planatol-Werk or Gerhards-Dosiertechnik and is illustrated by FIG. 4. Essential components of such equipment are a heatable preheating and heating tank 1 from which the warm material to be dosed is brought into heatable high pressure hoses 3 with the aid of geared pumps 2 projecting into the tank and under regulatable pressure and bypass control. The equipment can have one or more outlets for hose connections. There can be a pressure of up to 160 bar in the hoses. The hoses issue into heatable dosing heads 4, which are equipped with spring-mounted ball valves and nozzles 5. By using controlled compressed air valve opening and closing cycles calculated in milliseconds are obtained and as a function of the pressure upstream of the valve the same amount of material is always discharged for the same pressures and opening times. Any cobwebbing of the materials to be processed can be prevented by different nozzle sizes and temperature changes at the dosing heads. In addition to nozzles constructed as injection needles, it is also possible to use conical, double and multiple, as well as surface nozzles. Regulating and control electronics 6 ensure the monitoring and respecting of predetermined pressure and temperature values. By means of synchronizing circuitary the speed of the geared pumps and a belt carrying the forms can be matched to one another.

In order to completely fulfil the purposes of the present invention, modifications are made on the basic equipment, which e.g. make it possible to arrange the injection heads in such a way that there can be several injection shots per form on the forms sliding by. They are also installed in a movable manner, so that it is possible to take charge samples for analytical purposes, e.g. for determining the homogeneity of the charge or the injection shot weight.

As several injection heads are simultaneously used and controlled by a central unit, it is easily possible to fill 100,000 or more forms per hour. A limitation of the output rate is only provided by the mechanical advance of the cavities or forms and each individual nozzle can perform more than 1,000 cycles per minute. Thus, this type of filling system permits a much higher output rate than the equipment hitherto used for the filling of preshaped cavities or forms.

The dosing accuracy of the injection heads can be checked by separate removal from the filling line and separate injection into a weighing dish. For a production rate of 70,000 filled deep drawn cavities per hour with a filling weight of 500 mg, a dosing accuracy $<\pm2\%$ and a relative standard deviation of $<1\%$ were found. Laetus equipment, which checks each form for precise filling, can be used for a continual inspection during the filling process. It is also possible to pass the sealed strips over a $\pm$ balance.

As a result of the above-described inventive procedure, it is possible to process highly concentrated solutions or suspensions of active substances with little carrier substance, whilst filling can still take place with great accuracy. In the case of highly viscous solutions or suspensions, the aforementioned sedimentation tendency is largely eliminated. The filling equipment makes it possible to process materials with viscosities above 500,000 mPa.s. Thus, individual dosage forms of small, space-saving type and which are easy to swallow are obtained.

Figure 1A:
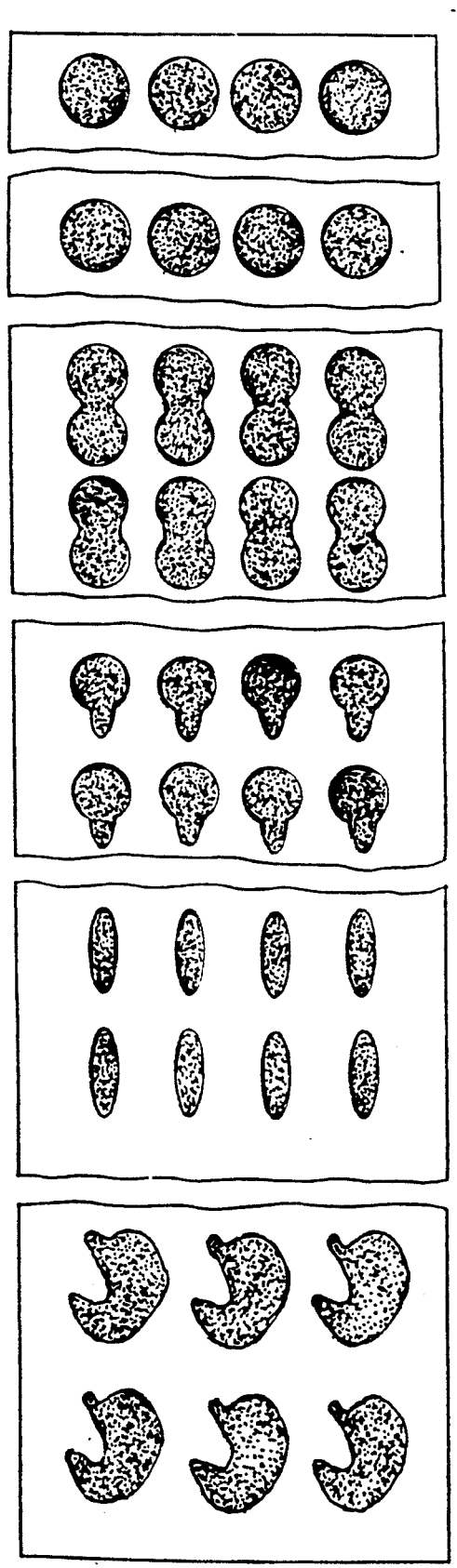
FIG. 1a is a plan view of the product of the present invention, which shows various shapes of the administration forms.
Figure 1B:
Figure 2A:
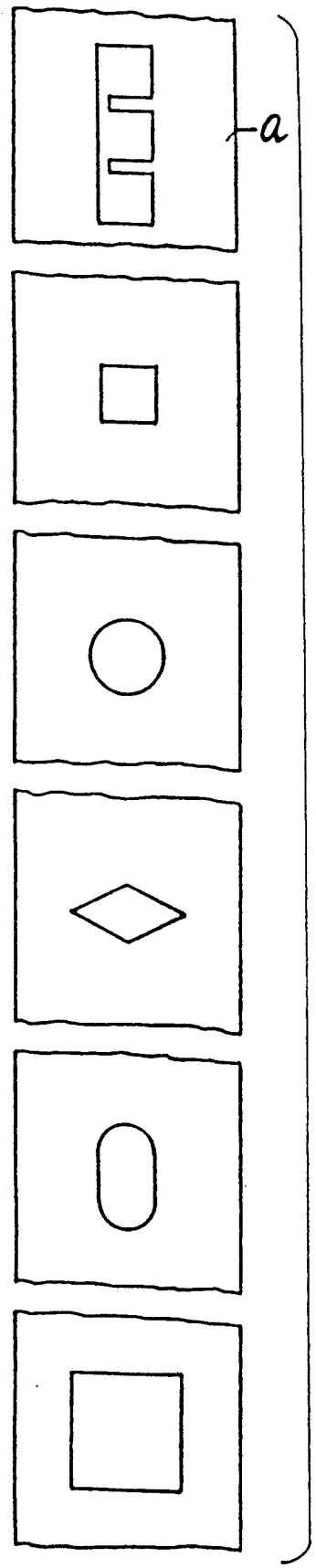
FIG. 2a shows a plan view of a foil with the different administration forms thereon.
Figure 2B:
FIGS. 2b and 2c show perspective views of administration forms.
Figure 2C:
Figure 2D:
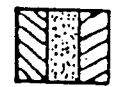
Figure 2E:
Figure 2F:
Figure 2G:

With the aid of the aforementioned dosing procedure, it is possible to produce dosage forms, which in the simplest case can be injection moulded without any mould on a substrate, either cooled, at ambient temperature or heated to above this and either stationary or in moving form. The viscosity and temperature of the materials to be processed then determine the shape of the desired article. This either leads to flat "lozenges" with a tablet-like appearance or cap-shaped products. If the substrate, e.g. a conveyor belt, is moved during the injection process, then small bars or strips are obtained. By simultaneously moving the spraying head in different directions, e.g. with the aid of an eccentric disk, the most varied product shapes are obtained and which can e.g. assume the shape of internal organs, such as the heart or stomach and in this way can refer to the particular indication range of the product produced. (FIGS. 1a and 1b).

Logically following the inventive principle, a further embodiment of the process proceeds in such a way that blister packs are filled. Blisters or "cupules" are drawn out of foils and films of the most varied type and these are filled and sealed with a cover film or foil, which is generally of coated aluminum. The enclosed formulation material is pressed by the cover foil and is consequently available. This development of the inventive process also makes it possible to produce many different shapes and sizes of the different administration forms (FIGS. 2a to 2g). Appropriately the blisters are given a slightly conical shape to facilitate the pressing out of the product.

The most appropriate use of the inventive process is constituted by the filling of hollow forms or cavities, i.e. forms of any shape and size which are closed all round, except for a feed funnel.

For producing these cavities, it is possible to use essentially all commercially available shapeable and sealable films and foils a, provided that they are compatible with the content to be introduced. Particularly suitable are thermoplastics, such as preferably polyethylene-coated PVC, PP or PVDC films, together with plastic-coated aluminium foils, provided that they can be shaped to the desired hollow form. It is also possible to use papers coated with plastics. Special colours or coatings of the films can make the enclosed product light, moisture or oxidation-proof. The films can be printed or marked in some other way for identifying the product. The term films is intended to cover all materials which can be used for the present purpose of forming hollow forms or cavities from films, i.e. apart from plastic films, also metal foils as well as coated paper and cardboard materials and the like.

Numerous different procedures can be used for producing the cavities. The subsequently described processes only constitute preferred examples. Using moulds, symmetrical or asymmetrical half-cavities can be produced from two films, which have to be welded together in a tight manner at their edges. Initially a funnel-shaped opening remains in the upper part of the cavity and is used for introducing the formulation material. The filling opening is sealed in conventional manner following the filling process and this gives an all round tight pack. Shaping and filling can be performed in such a way that the individual cavities are attached in the form of several "strips", from which the user can separate an individual dose. The product placed in the cavity is exposed by the tearing apart of the films.

In individual cases, it can be particularly advantageous if the films have a small, unsealed area, in which one film projects over the other by a few millimeters. This overlap makes it easier to separate the films.

Figure 3A:
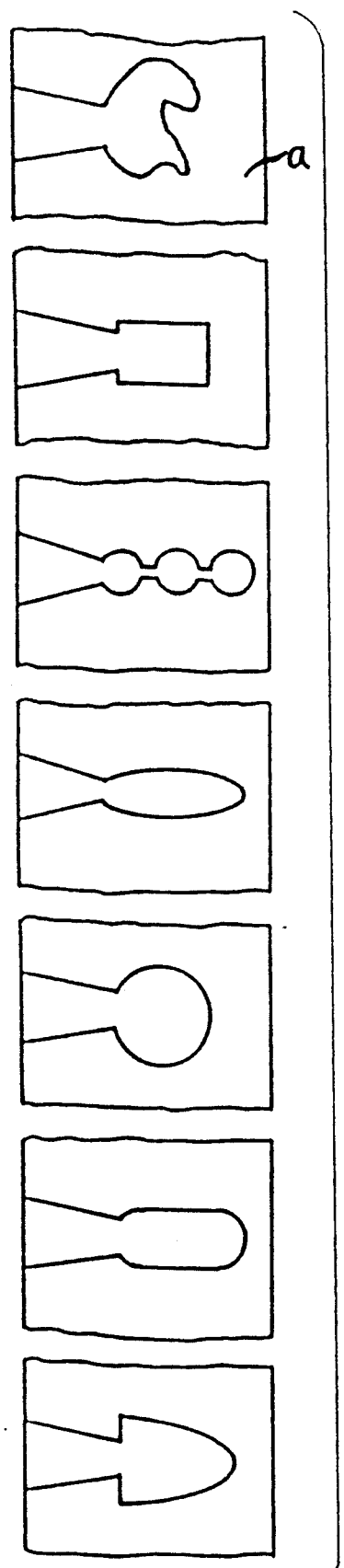
FIG. 3a is a plan view of the foil or film with individual cavities.
Figure 3B:

The individual cavities can e.g. be provided with constrictions, which permit a subsequent division, i.e. portioning of the product, e.g. for a child's dose or portions of a solid article for a three times daily dose (FIGS. 3a to 3b).

FIGS. 1a and 1b gives a number of examples for the administration forms or their cavities obtained according to the invention.

The inventive procedure for producing shaped blanks without any mould-dependent shaping and filling of blister packs and preshaped hollow forms is now to be supplemented by a description of the substances and materials, which as formulation materials differ entirely from the known suppository formulations or the materials given in DE-OS 27 10 307. In addition, vital advantages of the invention compared with the known administration forms will be explained.

Whereas the charges for filling suppository forms or those according to DE-OS 27 10 307 are preferably relatively low-melting fats, according to the inventive process suitable substances for basic formulations can e.g. be raw materials belonging to the gel forming agents. In heat, these form sols with water, other solvents and/or plasticizers. Dissolving of the gel forming agents can take place at temperatures above 100° C. Further adjuvants and active substances can be incorporated, generally by kneading into the cooled solution. At ambient temperature, the viscosity is between 50,000 and 800,000 mPa.s.

The articles obtained with the aid of the described dosing equipment are elastic, break-proof and suitable for swallowing, sucking, chewing or for buccal or perlingual application. They do not melt like fats at body temperature and instead decompose or dissolve in the body fluids at a planned varying speed. If water is used for mixing purposes, this can either be left in the formulations or the articles can be dried to a certain moisture content, e.g. in air conditioning cabinets, so that the hardness and elasticity can be controlled.

As a function of the solubility of the adjuvants and active substances, there are differing, controllable releases of the active substances, whilst there can be considerable variations as regards the nature and quantity of the adjuvants. This makes it possible to easily produce articles with a marked retarding action.

A particular administration form obtainable according to the invention are those products which are resistant to the gastric juices. By incorporating into the basic formulations substances or substance mixtures which do not dissolve in gastric juice, or through the exclusive use of such substances or substance mixtures, it is possible to obtain products able to withstand the gastric juice resistance tests given in pharmacopeias.

Figure 3C:
Figure 3D:
Figure 3E:
Figure 3F:
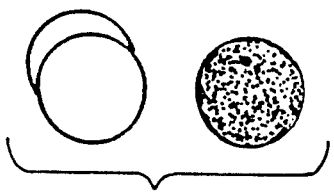
Figure 3G:
Figure 3H:
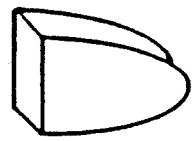

The inventive administration forms also make it possible to produce products, in which the initial dose and retard form are in one dose. A special example of this is constituted by the soporific chloral hydrate, which is a rapidly, but briefly acting hypnotic. To make it unnecessary for the patient to take this medicament twice or more during the evening or night and so as to permit uniform deep sleep, it is desirable to guarantee a roughly eight hour sleeping period by a single dose during the evening, without there being any hangover effect the following morning. Thus, according to the invention two or three chloral hydrate-containing formulations with different release characteristics are produced and successively injected in superimposed manner into the hollow form or cavity. The product then looks like that of FIG. 3C and the different layers can be made clear e.g. through different colourings of the individual formulations. A further development of this idea is the processing of fundamentally incompatible substance combinations, such as can e.g. occur in vitamin-mineral mixtures. The first injection shot introduces the vitamin formulation, the second a neutral formulation as a protective coating and finally the third shot introduces the mineral formulation giving an identical layer effect to that of FIG. 3C. It is obvious that the basic formulations in this case must coalesce to give a single solid article. It was pointed out hereinbefore that no difficulties arise when arranging the individual injection heads of the filling system for such injection sequences. It is obvious that the information given in connection with the above example is to be considered in general terms, i.e. for producing layered administration forms according to the invention.

Products suitable for buccal or sublingual administration can be produced in many different forms and compositions according to the basic principle of the invention. Thus, for example, spherical bodies with a small surface or elongated strips with a large surface can be shaped. Readily soluble or almost insoluble substances or mixtures can be used for producing the medicament, as a function of the desired residence time in the mouth. An important advantage of the invention is that slimy substances can be processed, which adhere for a long time to the mucous membrane of the mouth and consequently permit close contact with the mucous membranes of the active substance to be applied.

A further possibility of use of the present invention is the production of chewing and sucking articles, whose solubility can fluctuate between fast and "chewing gum-like". It is e.g. possible to embed substances, which are known as mouth and throat disinfectants or astringents, or as breath fresheners. It is also possible to embed in the basic formulation insoluble substances, which have a certain abrasive effect and serve to clean the teeth when chewing. Chewable antacids, which as viscous suspensions are attached to the mucous membrane of the stomach in film-forming manner, constitute a further field of use of the chewing products obtainable according to the invention. In this example the superiority of the administration forms of the present invention become particularly apparent. The hitherto known chewable antacids were constituted by tablets, which disintegrated in crumbling manner during chewing. The individual particles irritate the throat leading to coughing. In the case of the forms according to the invention, a viscous suspension forms in the mouth and which can be swallowed without irritating the mucous membranes.

According to the invention it is also possible to fill emulsions, e.g. of the W/O or O/W type, which decompose in the presence of body juices to finely disposed droplets and consequently facilitate the resorption of oils and fats and substances possibly dissolved therein. Naturally these emulsions must solidify below approximately 40° C. in order to be able to remove them from the cavities.

The invention also makes it possible to add to the dosage forms to be produced substances which are necessary for ensuring or obtaining a special pH or HLB value. The substances can e.g. be buffer mixtures or emulsifiers with a specific HLB value.

Unlike in the case of gelatin capsules, in which the filling with enzymes is problematical, these can easily be processed in the products obtainable according to the invention, because there is no need to use coatings or adjuvants which are attacked by the enzymes and which therefore reduce enzyme activity.

Another advantage of the invention is that the processing of oily substances, normally reserved for soft gelatin capsules, is readily possible by applying the oil to a carrier. This mixture is then injected together with a gel forming agent to give cavities which have no tendency to "bleed" or leak. This makes it possible to also process aqueous solutions, which is not conceivable for hard and soft capsule fillings.

It is not claimed that the above list of possible uses for the inventive administration forms is complete and it can in fact be extended at random. Specific statements are to be considered in general terms in the sense of the invention.

The following substances and representatives of substance classes or carrier materials can be advantageously used for the inventive process and applications: albumins, gelatins, casein, plant proteins, zein, lecithins, agar, gum Arabic, pectins, alginates, xanthan, natural and modified starches, maltodextrin, methyl cellulose, ethyl cellulose, cellulose ether polysaccharides, carboxymethyl celluloses, etherified carboxymethyl celluloses, hydroxypropyl cellulose, hydroxypropylmethyl cellulose phthalate, cellulose acetate phthalate, polyvinylacetate, polyvinylacetate phthalate, polyvinylalcohol, polyvinylpyrrolidone, polyacrylic acid, methacrylic acid and methacrylate polymers, polyethylene glycols, polyoxyethylene-polyoxypropylene polymers (Poloxalcol), triglycerides, partial glyceride mixtures, ethoxylated partial glycerides, long-chain fatty acids and their salts, silicones, colloidal silicic acid, bentonites, etc.

Substances usable as plasticizers are e.g. glycerol, propylene glycol, polyethylene glycols, acetyltributyl citrate, triacetin, dibutyl tartrate, dibutyl phthalate, sorbitol, sorbitan mixtures, glucose syrup, etc.

For reasons of completeness it is pointed out that it is also possible to add to inventively obtainable products additives, such as e.g. opacifiers, dyes, flavours, sweeteners, preservatives and the like.

It is important for the invention that the aforementioned materials are so matched in preparing a formulation material that the adhesion between the solidified formulation material and the internal surface of the hollow form or cavity is reduced to a minimum. In most cases standard thermoplastics and carriers or formulation masses permit a clean separation. However, if this is not possible in individual cases, the invention provides advantageous aids, to which reference will be made hereinafter.

If necessary, it is possible according to the invention to provide the cavities with separating coatings prior to the filling with the formulation material, in order to prevent sticking or adhesion between the film surface and the formulation material or at least reduce it to a minimum. Preferably the formulation material/separating agent pairs have the affinity pairs lipophilic/lipophobic or hydrophilic/hydrophobic. Preferred substances for this purpose are e.g. talc, starches and the like. It is also possible to atomize or spray into the cavity separating agents, such as oils, fats or silicones. Finally such substances can also be applied to the inner wall by using brush-like, rotary tools, which spread within the cavity. The same applies with respect to deep-drawn packs.

It can be advantageous to apply the separating agent to one side of the starting film prior to the removal of the hollow cavity and said prepared side subsequently forms the inner surface of the cavity.

However, the above-described coating procedures also make it possible to apply those coatings to the inner wall of the cavity which do not function as a separating medium, but instead serve as a carrier coating for lubricants or dyes, flavours, sweeteners, preservatives and the like and which inter alia favourably influence the application or administration of the product. This carrier coating is joined to the introduced formulation material and is placed like a jacket round the solid article. This ensures that only the outer coating of the product is e.g. coloured or aromatized, which greatly reduces corrigents, which would otherwise have to be homogeneously distributed in much larger quantities in the complete charge.

The invention clearly leads to many advantages. Thus, it permits the cost-saving and environmentally beneficial production of orally usable administration forms not suffering from the disadvantages referred to hereinbefore. Thus, inexpensive products are made available, which can be readily produced in very large numbers. It is possible to use an almost unlimited number of different formulations for different indications. Inherently incompatible substances can be present in a single administration form without reacting with one another. It is also possible to process side by side and in large numbers adjuvants, such as e.g. solid and liquid substances which influence the solubility of an active agent, so that planned active substance releases are brought about.

The description of the inventive process makes it clear that the obligatory shaping process for many administration forms is rendered superfluous, because the pack simultaneously forms the shaping element. Thus, there are no packaging problems with respect to the supply of the objects to the packaging machines or with respect to dimensional tolerances, such as have been hitherto unavoidable in the case of soft gelatin capsules. There is no possibility of intermixing of "foreign bodies", such as foreign dragees or capsules, such as can occur in the hitherto known processes during production or packaging, because the product is introduced directly in the liquid state into the pack and the filling opening is sealed. By special shaping of the film, form and content, it is possible to exclude confusion with respect to the products.

The invention also makes it possible to process a very large number of substances side by side, i.e. adjuvants or active substances on the one hand, or solid and liquid substances on the other. This can lead to products with a controlled active substance release, as well as to gastric juice-resistant products. It is also possible to produce chewing and sucking articles.

Many of the novel products, to the extent that they are not designed as sucking or gastric juice-resistant products, as they are generally elastic, can be bit and swallowed in small fragments, without it being necessary to subsequently drink a liquid, which is a help in the case of patients having swallowing difficulties or who do not like to take tablets.

The invention also provides many economic advantages. Thus, the separate shaping stage is obviated, which in itself greatly reduces costs compared with known processes. The high output rate of filled and therefore simultaneously packed forms per time unit and the easily installed on-line process controls represent a further cost-saving rationalization. To the extent that the inventive process is also suitable as a substitute for all known conventional capsule production methods, it is possible to obviate the costs for expensive air conditioning plants and installations for recovering solvents. Since, unlike in capsule production, no raw material is wasted (approximately 50% wastage in soft capsule production and approximately 30% in hard capsule production), this also leads to a clear saving. Finally the inventive process can be performed without prejudice to the environment.

The following examples further illustrate the invention.

The most varied types of carriers can be combined in the most varied ways to obtain the different use purposes. The multiplicity of possibilities of the inventive process can only be intimated by the examples.

EXAMPLE 1

| Gelatin | 120 g |
| 70% sorbitol solution | 180 g |
| Water | 373 g |
| Water-soluble protein hydrolyzate | 600 g |
| Sorbic acid | 5 g |
| Caramel | 12 g |
| Meat extract flavour | 10 g |
| | 1300 g |

The gelatin is dissolved in vacuo at 70° C. in the solution of sorbic acid in water. The flavor, caramel, sorbitol solution and protein hydrolyzate are successively incorporated into this solution. The mixture is vented in the heat. At 56° C. and 48 bar, the material is injected or atomized into heaps of in each case 1300 mg on a substrate cooled to 10° C. Drying takes place at 20% relative humidity and ambient temperature until each individual dose weighs 1 090 mg.

EXAMPLE 2

| Decomposed, esterified starch (Emgum) | 120 g |
| Oxidized wheat starch (Emox) | 180 g |
| Sugar | 50 g |
| 75% glucose syrup | 175 g |
| Water | 200 g |
| Chlorhexidine | 6 g |
| Extractum Arnicae plv. subt. | 10 g |
| Citric acid:sodium citrate 1:1 | 20 g |
| Ginger flavour | 7 g |
| | 768 g |

The sugar, glucose syrup and water are heated to 110° C. until a clear solution is obtained. Both starch types are introduced, accompanied by vigorous stirring, into the solution cooled to 70° C. The mixture is briefly heated to 90° C. After cooling again to 70° C., the remaining substances are homogeneously incorporated in the rising order of their weights. At 70° C. and 90 bar and with a dosing head temperature of 85° C., the material is injected into blisters with a tablet-like depression. Each dose contains 750 mg. Sealing takes place with a peel-off film.

EXAMPLE 3

| Cardiac glycoside | 0.5 g |
|---|---|
| ethoxylated partial glyceride mixture of natural, saturated, even-numbered plant fatty acids (Softigen 767) | 100.0 g |
| Polyoxyethylene-polyoxypropylene polymer (Poloxalcol) | 700.0 g |
| Polyethylene glycol 400 (PEG) | 199.5 g |
| | 1000.0 g |

Accompanied by moderate stirring, the melted Poloxalcol kept at 60° C. is introduced into the PEG heated to 60° C. The solution of cardiac glycoside in Softigen heated to 45° C. is homogeneously stirred into the first solution. The material cooled to 45° C. is injected in 200 mg quantities at 22 bar into oval cavities cooled to 10° C. The cooled cavities can immediately be sealed.

EXAMPLE 4

| Gelatin | 240 g |
|---|---|
| Hydroxypropyl-methyl-cellulose phthalate (HP 55) | 90 g |
| Water | 389 g |
| 25% ammonia | 21 g |
| 85% glycerol | 260 g |
| | 1000 g |

The homogeneous powder mixture of gelatin and H$^P$ 55 is rapidly introduced, accompanied by stirring, into the mixture of water and ammonia. It is important for all the powder particles to be uniformly wetted. Following a swelling time of 12 minutes at ambient temperature, the crumbly material is melted in vacuo at 90° C. The glycerol heated to 40° C. is stirred into the viscous material obtained. The cooled material is a basic material for a gastric juice-resistant administration form. By dying the material during production, e.g. with erythrosine, it is possible to show that dosed portions are resistant for 2 hours to artificial gastric juice (0.1n HCl) without bleeding, whilst after transfer into a buffer solution (0.2 m Na$_2$HPO$_4$ solution 773 ml+0.1 m citric acid solution 227 ml; pH 6.8), they dissolve uniformly and without leaving a residue within 26 minutes.

By incorporating filling materials, e.g. corn starch into the basic formulation the gastric juice resistance is retained, whilst the solubility in artificial intestinal juice can be controllably extended to several hours.

EXAMPLE 5

| Gelatin | 240 g |
|---|---|
| Cellulose-acetate phthalate (CAP) | 90 g |
| Water | 410 g |
| 85% glycerol | 260 g |
| | 1000 g |

This formulation is prepared in the same way as example 4 and the behavior of the dosed portions correspond to those of example 4.

EXAMPLE 6

| Polyvinylpyrrolidon (PVP) (Kollidon 30) | 50 g |
|---|---|
| Oxidized starch (Emox 170) | 250 g |
| 85% glycerol | 250 g |
| Water | 230 g |
| Maltodextrin | 480 g |
| Diphenhydramine-HCl | 10 g |
| Fennel-honey flavour | 10 g |
| | 1280 g |

The water and glycerol are mixed. The PVP is introduced into the cold solution and stirred until completely dissolved. Accompanied by stirring, the maltodextrin is firstly dissolved in the solution heated to 95° C., followed by the stirring in of the starch, also at 95° C. The diphenhydramine and the flavour are homogeneously incorporated into the mixture cooled to 75° C. The material is filled in 1280 mg portions into blisters at 65° to 70° C. and 95 bar and immediately after the solidification of the material they are sealed with peel-off film.

We claim:

1. In a process for producing individually dosed administration forms in which a formulation material containing conventional additives and active substances, which is plastic at elevated temperature and which is based on a sol/gel ratio with a softening range above 37° C. is heated to above 37° C. and under pressure is brought into contact with a substrate and then cooled, the formulation material thereby being in a form suitable for administration, the improvement comprising transferring a warm formulation material which has a viscosity of more than 3,000 mPa.s to be dosed from a heating tank into a heated dosing apparatus which operates at high pressure, providing said heated dosing apparatus with compressed air valves which provide opening and closing cycles within the time of milliseconds, building up a uniform high pressure against said valves by pressure generating means, and discharging through a time-precisely limited opening of the valves, a constant quantity of the warm formulation material being thereby dosed onto the substrate, wherein in said discharge step the same amount of material is discharged under constant pressure each time and the valve opening times is a function of the pressure upstream of said valves.

2. Process according to claim 1, wherein said substrate is movable.

3. Process according to claim 1, wherein said substrate is stationary.

4. Process according to claim 1, wherein said pressure generating means are gear pumps.

5. Process according to claim 1, wherein the warm formulation material to be dosed is brought with the aid of pumps connected to the heating tank into high pressure hoses which are heated.

6. Process according to claim 5, wherein the heatable high pressure hoses extend into heatable dosing heads of said dosing apparatus, said dosing heads being equipped with spring-mounted ball valves and nozzles.

7. Process according to claim 1, wherein said formulation material is selected from the group including a formulation material having a controllable sustained release action, a formulation material having a gastric juice resistance, and a formulation material for buccal or sublingual application.

8. Process according to claim 1, wherein a chewing or sucking article is produced from the formulation material.

9. In a process for producing individually dosed administration forms in which a formulation material containing conventional additives and active substances, which is plastic at elevated temperature and which is based on a sol/gel ratio with a softening range above 37° C. is heated to above 37° C. and under pressure is introduced into blisters or cavities produced from films and then cooled, the formulation material thereby being in a form suitable for administration, the improvement comprising transferring a warm formulation material which has a viscosity of more than 3000 mPa.s to be dosed from a heating tank into a heated dosing apparatus which operates at high pressure, providing said heated dosing apparatus with compressed air valves which provide opening and closing cycles within the time of milliseconds, building up a uniform high pressure against said valves by pressure generating means, and discharging through a time-precisely limited opening of the valves, a constant quantity of the warm formulation material being thereby dosed into the blisters or cavities produced from films, wherein in said discharge step the same amount of material is discharged under constant pressure each time and the valve opening times are a function of the pressure upstream of said valves.

10. Process according to claim 9, wherein said pressure generating means are gear pumps.

11. Process according to claim 9, wherein the warm formulation material to be dosed is brought with the aid of pumps projecting into the heating tank and with regulatable pressure and bypass control into heatable high pressure hoses.

12. Process according to claim 11, wherein the heatable high pressure hoses extend into heatable dosing heads, which are equipped with spring-mounted ball valves and nozzles.

13. Process according to claim 9, wherein films for forming cavities have an unsealed zone, in which one film projects over another by a few millimeters.

14. Process according to claim 9, wherein an adhesion-reducing separating agent is placed on the inner surface of a cavity or a blister.

15. Process according to claim 14, wherein the formulation material and the separating agent have opposite affinities.

16. Process according to claim 14, wherein said formulation material is selected from the group including a lipophilic and hydrophobic formulation material, and wherein water is atomized into the cavity or blister prior to the introduction of said formulation material thereinto.

17. Process according to claim 14, wherein said formulation material is hydrophobic and wherein an inner surface of the cavity or blister is coated with hydrophobic oils.

18. Process according to claim 9, wherein the cavity or blister comprises a thermoplastic material selected from the group consisting of thermoplastic-coated aluminum and plastic-lined paper.

19. Process according to claim 9, wherein prior to a removal of the cavity or blister from a film a separating agent is applied to one side of the film to be shaped into said blister or cavity, said side subsequently constituting an inside of the cavity or blister.

20. Process according to claim 9, wherein agents favorably influencing the application and acceptance of a finished formulation material are applied to an inner surface of the cavity or blister.

21. Process according to claim 20, wherein the agents are selected from the group comprising dyes, flavors, sweeteners, preservatives and lubricants.

22. Process according to claim 9, wherein one of the cavities and blisters are successively filled with different formulation materials.

23. Process according to claim 22, wherein one of said different formulation materials has effect immediately after consumption and another of said materials shows a retarded effect after consumption of an administration form.

24. Process according to claim 9, wherein said formulation material is selected from the group including a formulation material having a controllable sustained release action, a formulation material having a gastric juice resistance and a formulation material for buccal or sublingual application.

25. Process according to claim 9, wherein a chewing or sucking article is produced from the formulation material.

* * * * *